United States Patent
Seki et al.

(10) Patent No.: US 8,242,295 B2
(45) Date of Patent: Aug. 14, 2012

(54) PROCESS FOR PRODUCING FATTY ACID ALKYL ESTERS AND GLYCERIN

(75) Inventors: Yuichiro Seki, Wakayama (JP); Nobuhiro Tatsumi, Wakayama (JP); Takanobu Katayama, Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 12/091,306

(22) PCT Filed: Dec. 19, 2006

(86) PCT No.: PCT/JP2006/325694
§ 371 (c)(1),
(2), (4) Date: Apr. 24, 2008

(87) PCT Pub. No.: WO2007/072972
PCT Pub. Date: Jun. 28, 2007

(65) Prior Publication Data
US 2009/0156846 A1   Jun. 18, 2009

(30) Foreign Application Priority Data
Dec. 20, 2005   (JP) ................... 2005-365840

(51) Int. Cl.
*C11C 3/00*   (2006.01)
*C07C 27/04*   (2006.01)

(52) U.S. Cl. ........ 554/169; 554/163; 554/170; 554/174; 568/885; 568/877

(58) Field of Classification Search ............ None
See application file for complete search history.

(56) References Cited

U.S. PATENT DOCUMENTS

| 4,698,186 A | 10/1987 | Jeromin et al. |
| 4,965,236 A | 10/1990 | Roberts |
| 5,157,168 A | 10/1992 | Wilmott et al. |

(Continued)

FOREIGN PATENT DOCUMENTS

EP   0 623 581   7/1999

(Continued)

OTHER PUBLICATIONS

Canakei M. et al., Biodiesel Production via Acid Catalysis, 1999, Americna Society of Agricultural Engineers, vol. 45 (5), pp. 1203-1210.*

(Continued)

*Primary Examiner* — Yate K Cutliff
(74) *Attorney, Agent, or Firm* — Oblon, Spivak, McClelland, Maier & Neustadt, L.L.P.

(57) ABSTRACT

Disclosed is a process for producing a fatty alkyl ester and glycerin, including step 1 of reacting fats and oils with C1 to C5 lower alcohols, step 2 of removing the lower alcohols discharged from the outlet of a rector in step 1 until the lower alcohol content is reduced to 8 wt % or less, step 3 of separating the product obtained in step 2 into oil and aqueous phases, step 4 of reacting the oil phase obtained in step 3 with lower alcohols in the presence of an acid catalyst, and step 5 of separating the product discharged from the outlet of a reactor in step 4 into oil and aqueous phases thereby giving fatty acid alkyl esters and glycerin, as well as a process for producing fatty alcohols from hydrogen and the fatty acid alkyl esters obtained in the above process.

19 Claims, 1 Drawing Sheet

U.S. PATENT DOCUMENTS

| | | | |
|---|---|---|---|
| 5,440,027 A | 8/1995 | Hasenhuettl | |
| 5,849,939 A | 12/1998 | Mittelbach et al. | |
| 6,288,251 B1 * | 9/2001 | Tsuto et al. | 554/169 |
| 2004/0034244 A1 | 2/2004 | Bournay et al. | |
| 2004/0133049 A1 | 7/2004 | Pelzer et al. | |
| 2005/0113588 A1 * | 5/2005 | Hillion et al. | 554/174 |
| 2005/0113589 A1 * | 5/2005 | Katayama et al. | 554/174 |

FOREIGN PATENT DOCUMENTS

| | | |
|---|---|---|
| EP | 1 211 236 | 6/2002 |
| EP | 1 460 124 | 9/2004 |
| FR | 2 743 084 | 7/1997 |
| GB | 795 573 | 5/1958 |
| JP | 56 65097 | 6/1981 |
| JP | 06-313188 * | 11/1994 |
| JP | 2001-79413 | 3/2001 |
| JP | 2002-265620 A | 9/2002 |
| JP | 2003-128827 A | 5/2003 |
| JP | 2003-146826 A | 5/2003 |
| JP | 2003-277417 A | 10/2003 |
| JP | 2004-043557 A | 2/2004 |
| JP | 2005-139322 A | 6/2005 |
| JP | 2005-200398 | 7/2005 |
| JP | 2006-008659 A | 1/2006 |
| JP | 2006-008757 A | 1/2006 |
| JP | 2006-161027 A | 6/2006 |
| WO | 2005 021697 | 3/2005 |

OTHER PUBLICATIONS

Kawakami et al., Production of Fatty Acid Esters, 1994, English Abstract of JP 06-313188 (1 page).*

Chinese Office Action issued Jul. 28, 2010, in correponding Chinese Patent Application No. 200680048338.8 (with English language translation.).

Office Action mailed Jan. 31, 2012 in Japanese Patent Application No. 2005-365840 (with English translation).

Office Action issued May 24, 2011 in Japan Application No. 2005-365840 (With English Translation).

* cited by examiner

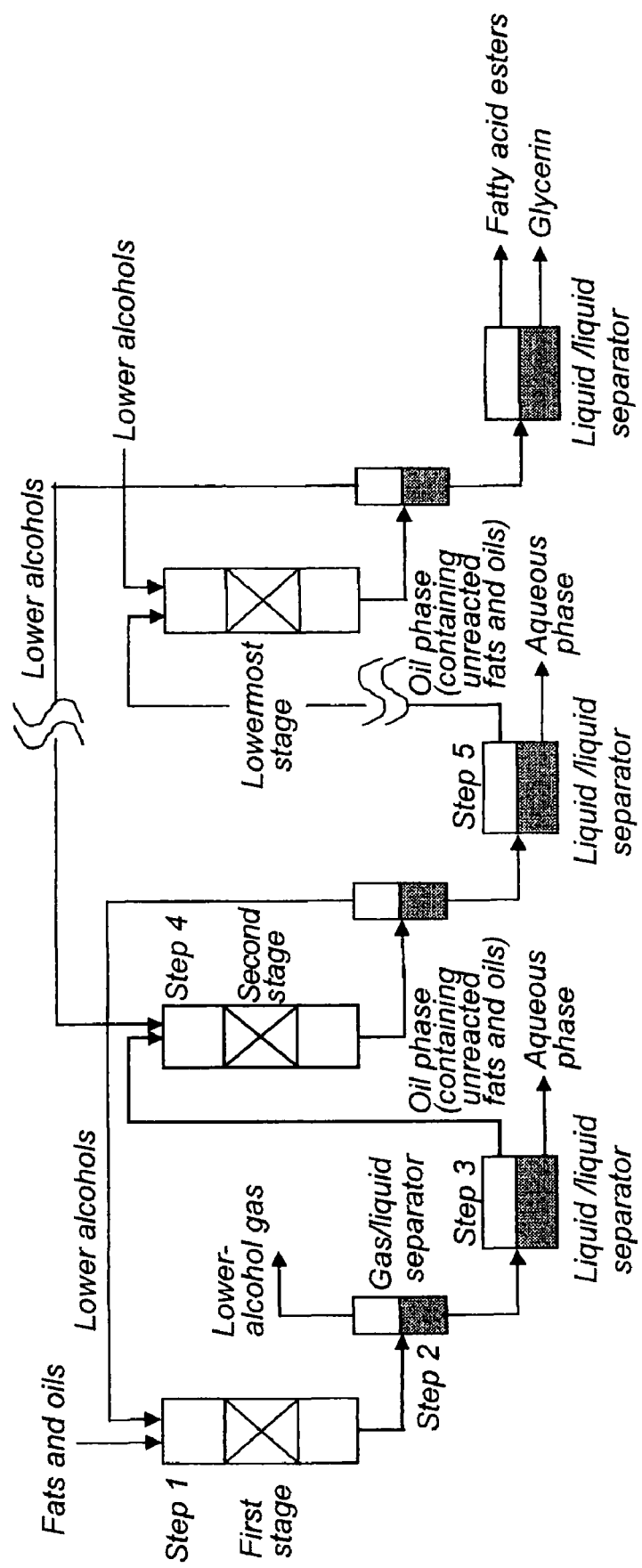

PROCESS FOR PRODUCING FATTY ACID ALKYL ESTERS AND GLYCERIN

FIELD OF THE INVENTION

The present invention relates to a process for producing fatty acid alkyl esters and glycerin from fats and oils and lower alcohols by using an acid catalyst.

BACKGROUND OF THE INVENTION

As methods of producing fatty acid alkyl esters by ester exchange between triglyceride-based fats/oils and lower alcohols, various methods are known. In such a reaction, for example JP-A 56-65097 shows that, while glycerin formed by a multi-stage reaction is separated, the reaction is promoted with use of an alkali catalyst.

To solve this problem, WO-A 2005/021697 has reported a process for producing fatty acid alkyl esters by using a solid acid catalyst.

SUMMARY OF THE INVENTION

The present invention provides a process for producing a fatty alkyl ester and glycerin, including:

step 1 of reacting fats and oils with a C1 to C5 lower alcohol;

step 2 of removing the lower alcohol from the outlet product of step 1 until the lower alcohol content is reduced to 8 wt % or less;

step 3 of separating the product obtained in step 2 into an oil phase and an aqueous phase;

step 4 of reacting the oil phase obtained in step 3 with a lower alcohol in the presence of an acid catalyst; and step 5 of separating the outlet product of step 4 into an oil phase and an aqueous phase to obtain an fatty acid alkyl ester(s) and glycerin.

The present invention also provides a process for producing a fatty alcohol (s) from hydrogen and the fatty acid alkyl ester obtained in the above process.

BRIEF DESCRIPTION OF THE DRAWING

FIG. 1 is a schematic view showing the pseudo-countercurrent operation used in the process of the present invention.

DETAILED DESCRIPTION OF THE INVENTION

A homogeneous catalyst is used in JP-A 56-65097. Neutralization/removal of the catalyst is therefore necessary after the ester-exchange reaction and purification of glycerin is complicated.

In WO-A 2005/021697, there arises another problem that methoxypropanediol is formed as a side product by reaction of glycerin with lower alcohols. This side product, upon partition of the glycerin and fatty acid alkyl esters into oil and aqueous phases, is partitioned together with the glycerin into the same phase, thus deteriorating qualities of the glycerin. However, there are no techniques concerning the inhibition of formation of this side product.

The present invention provides a method of obtaining glycerin and fatty acid alkyl esters highly efficiently in higher yield by inhibiting the side reaction of glycerin.

The present inventors found that in a process for producing fatty acid alkyl esters and glycerin from fats and oils, and lower alcohols, at multi-stages by using an acid catalyst, the reaction is promoted by the acid catalyst when the lower alcohols after conclusion of the reaction are removed under the optimum conditions, whereby the problem described above can be solved.

According to the present invention, fatty acid alkyl esters can be obtained highly efficiently in higher yield. Further, formation of methoxypropanediol as a side product of glycerin can be inhibited thus preventing deterioration in the qualities of glycerin and facilitating operation in a purification step.

[Step 1]

The fats and oils used in step 1 in the present invention include naturally occurring vegetable fats and oils and animal fats and oils. The vegetable fats and oils include coconut oil, palm oil, palm kernel oil etc., and the animal fats and oils include tallow, lard, fish oil etc.

Specific examples of the C1 to C5 lower alcohols used in step 1 in the present invention include methanol, ethanol, propanol etc., among which methanol is industrially preferable from the viewpoint of low cost and easy recovery.

From the viewpoint of attaining an excellent reaction rate, the necessary stoichiometric quantity of lower alcohols, in terms of the molar ratio of lower alcohols to fats and oils (calculated as triglycerides), is preferably 1.5 or more, more preferably 2 or more. From the viewpoint of effecting the reaction economically by reducing the amount of alcohols recovered, the molar ratio of lower alcohols to fats and oils is preferably 50 or less, more preferably 30 or less, even more preferably 15 or less. If necessary, the fats and oils may be diluted with a diluent. The diluent includes, but is not limited to, xylene, toluene, hexane, tetrahydrofuran, acetone, ether, and fatty acid alkyl esters.

The reaction in the step 1 may be carried out in the absence of a catalyst, but preferably a homogeneous or heterogeneous catalyst known in the art is used. As the homogeneous catalyst, an alkali catalyst such as NaOH can be preferably used. The heterogeneous catalyst is not particularly limited insofar as it is a catalyst having alcoholysis reaction activity, and examples thereof include sodium carbonate and sodium bicarbonate as described in JP-A 61-254255 and crystalline titanium silicate, crystalline titanium aluminum silicate, amorphous titanium silicate and their corresponding zirconium compounds as described in EP0623581B1. In a preferable mode, the weakly acidic, acid catalyst described in detail in step 4 is used.

The reaction temperature in step 1 is preferably 50° C. or more, more preferably 60° C. or more, even more preferably 80° C. or more, from the viewpoint of attaining a sufficient catalyst activity to increase the reaction rate and of effecting the reaction economically by controlling the necessary volume of a reactor for attaining the desired rate of reaction. The reaction temperature in step 1 is preferably 230° C. or less, more preferably 200° C. or less, from the viewpoint of improving the yield of glycerin by inhibiting the formation of ethers as side products between glycerin and lower alcohols.

The reaction system in step 1 may be either a batch or continuous system and may be a vessel type reactor having a stirrer or a fixed bed reactor packed with a catalyst and is preferably a fixed bed reactor from the viewpoint of eliminating the necessity for separation of the catalyst.

When the reaction is carried out in the vessel type reactor, the amount of the catalyst used is preferably 1 wt % or more, more preferably 3 wt % or more, even more preferably 5 wt % or more, based on the fats and oils, from the viewpoint of attaining sufficient activity to complete the reaction in a short time. From the viewpoint of keeping a sufficiently suspended state under stirring, the amount of the catalyst used is preferably 20 wt % or less, more preferably 17 wt % or less, even more preferably 15 wt % or less, based on the fats and oils. The reaction is carried out usually at normal pressures, but may be carried out under increased pressure or under reduced pressure. Under a reduced pressure, a gas/liquid/solid reaction can be carried out by gasifying an alcohol at a temperature not higher than the boiling point at the atmospheric pressure of the used alcohol. Under an increased pressure, on the other hand, a liquid/liquid/solid reaction can be carried out by preventing the alcohol from evaporating at a temperature not lower than the boiling point at the atmospheric pressures of the alcohol.

When the reaction is continuously carried out in a fixed bed reactor, the liquid hourly space velocity (LHSV) based on the fats and oils is preferably not lower than 0.02/hr, more preferably not lower than 0.1/hr, from the viewpoint of increasing productivity per unit volume of the reactor to effect the reaction economically. The reaction pressure is 0.1 to 10 MPa, more preferably 0.5 to 8 MPa. When the reaction is carried out in a liquid/liquid/solid system, the reaction pressure is established according to the vapor pressure and reaction temperature of the lower alcohols.

When fixed bed reactors are used, the method of feeding lower alcohols in the present invention is conducted preferably a method carried out by pseudo-countercurrent operation which is co-current operation in each of the fixed bed reactors but is judged to be countercurrent operation in view of the facilities as a whole. The outline of the pseudo-countercurrent operation is shown in FIG. 1.

That is, the method is preferably carried out in pseudo-countercurrent operation wherein multistage fixed bed reactors each packed with a solid acid catalyst are arranged, and fats and oils are fed to a reactor at an upper stage, preferably at the uppermost stage and then sent to a stage at the downstream side preferably one after another while feeding liquid lower alcohols to a reactor at a lower stage, preferably at the lowermost stage and returning liquid lower alcohols discharged from the outlet of the reactor to a stage at the upstream side preferably one after another. As used herein, "a stage at the upstream side" refers to a stage nearer to the fixed-bed reactor to which starting fats and oils are first fed, while "the uppermost stage" refers to a stage at the uppermost side. That is, a plurality of fixed bed reactors each packed with a solid acid catalyst are arranged at multi-stages in series, and fats and oils are fed to a reactor at an upper stage, preferably at the uppermost stage and then sent to lower stages preferably one after another, while liquid lower alcohols are fed to the top of a reactor at a lower stage, preferably in the lowermost stage and contacted in co-current downward flow with the liquid (fats and oils) from an upper stage, and then liquid lower alcohols after separation are fed to the top of a reactor at an upper stage and contacted with fats and oils in co-current downward flow in the same manner as above. This operation is conducted repeatedly whereby the fats and oils are sent from the upper to lower stages while the alcohols are sent from the lower to upper stages so that in view of the entire facilities, it seems as if countercurrent operation was conducted (pseudo-countercurrent operation) although co-current operation is actually conducted in individual reactors. In this embodiment, therefore, the amount of the lower alcohols fed can be reduced economically advantageously, while the amount of the remaining fats and oils can be reduced and the yield of the desired products i.e. fatty acid alkyl esters can be increased. In this case, the direction along which the liquid flows in each fixed bed reactor may be either a co-current downflow or a co-current upflow. More specifically, the reaction in the fixed bed reactor system may be the reaction of three phases i.e. liquid (alcohols)/liquid (fats and oils)/solid (catalyst) where the alcohols such as methanol are contacted in a liquid state or gas (alcohols)/liquid (fats and oils)/solid (catalyst) wherein the alcohols have been gasified, and in the reaction in the liquid/liquid/solid system, the two liquids may be allowed to flow upward or downward and thereby contacted with each other. In the reaction in the gas/liquid/solid system, they may be contacted with one another in either a gas-liquid co-current system or a gas-liquid countercurrent system.

[Step 2]

Step 2 is a step of removing the lower alcohols discharged from the outlet of a rector in step 1 until the lower alcohol content is reduced to 8 wt % or less, preferably 5 wt % or less, more preferably 2 wt % or less. By reducing the lower alcohols to the desired concentration, formation of methoxypropanediol as a side product in step 4 can be preferably inhibited.

The method of removing the lower alcohols is not particularly limited, and a known method can be used. For example, the product from the outlet of the reactor in step 1 is passed through an evaporator, whereby the lower alcohols in the product can be separated until their content is reduced to 8 wt % or less. The evaporation is carried out at pressure and temperature at which the content of the lower alcohols in the liquid reaction product from the outlet of the evaporator is reduced to 8 wt % or less, preferably 5 wt % or less, more preferably 2 wt % or less. Specifically, when the product is to be flashed at ordinary pressure, the product discharged from the outlet of the reactor in step 1 may be previously heated prior to flashing, depending on the case. The method of removing the lower alcohols can be suitably modified for example by depressurizing the evaporation place.

The correlation of the concentration of lower alcohols with inhibition of formation of the side product methoxypropanediol is estimated as follows: That is, when the content of the lower alcohols in the reaction product is high, the next step (step 3) of separating the product into oil and aqueous phases is deteriorated in separation ability, and the concentration of glycerin in the oil phase is increased. As a result, a decrease in the reaction rate in the step 4 was found. That is, the reaction temperature should be increased in order to attain the same reaction rate as in the same reaction except that the glycerin is brought in a smaller amount into the system. However, the activation energy of the side reaction is greater than that of the main reaction, and thus when the temperature is increased, methoxypropanediol is formed as a side product in a larger amount, resulting in a decrease in the yield of the product glycerin. Alternatively, the reaction rate can be increased by increasing the volume of the catalyst, which however leads to higher costs. For the above reason, the removal of the lower alcohols until the desired concentration is attained in this step is important for obtaining fatty acid alkyl esters highly efficiently in higher yield and for inhibiting formation of methoxypropanediol as a side product of glycerin thereby preventing deterioration in the qualities of glycerin and facilitating operation in a purification step.

[Step 3]

The step 3 is a step of separating the product obtained in step 2 into oil and aqueous phases. The separation method is not particularly limited and the product can be separated by methods known in the art, such as separation by leaving the product (stationary separation) or condensation separation. The separation temperature is preferably 80° C. or less, more preferably 70° C. or less, even more preferably 60° C. or less. When the content of monoglycerides in the oil phase is high, the rate of separation is decreased due to emulsification, and thus the stationary separation requires a long time for separating the glycerin in the oil phase until the equilibrium solubility is reached. In this case, a condensation separator such as a coalesser filter is preferably used. The separated oil phase contains the fatty acid alkyl esters formed in step 1, the starting materials and reaction intermediate glycerides as the main components, as well as a very small amount of water, lower alcohols, glycerin etc. On the other hand, the aqueous phase contains glycerin, water and lower alcohols as the main components. The content of glycerin in the separated oil phase is preferably 1.2 wt % or less, more preferably 0.6 wt % or less, even more preferably 0.4 wt % or less, from the viewpoint of preventing the formation of methoxypropanediol as a side product.

[Step 4]

Step 4 is a step in which the reaction of fats and oils, and lower alcohols, not reacted in step 1, is allowed to proceed, and the mode of reaction and the operation in step 4 are the same as previously described in detail in step 1. However, the catalyst used is an acid catalyst, the feature of which is hereinafter described in detail.

The acid catalyst used in the present invention is preferably a solid acid catalyst. The solid acid catalyst includes simple or composite metal oxides, metal phosphates, natural minerals and layer compounds. The simple or composite metal oxides include, for example, niobic acid, $SiO_2$—$Al_2O_3$ etc., and the metal phosphates include $GaPO_4$ etc. The natural minerals and layer compounds include montmorillonite etc. The acid solid catalyst is preferable for easy separation of the catalyst. The catalyst is particularly preferably a weakly acidic catalyst, more preferably a catalyst having a strong acid point of not higher than 0.2 mmol/g-cat and a weak acid point of not less than 0.3 mmol/g-cat, each acid point being defined as follows:

Weak acid point: the point at which desorption of $NH_3$ occurs in the range of 100 to 250° C. in TPD (temperature programmed desorption: ammonia adsorption-desorption process)

Strong acid point: the point at which desorption of $NH_3$ occurs in the range of higher than 250° C. in TPD It is further preferable that the weakly acidic solid catalyst is a molded product of a weakly acidic solid catalyst having the structure (A), the structure (B) and the metal atom (C) as follows:

Structure (A): a structure of an inorganic phosphoric acid wherein the hydrogen atom is removed from at least one OH group thereof, Structure (B): a structure of an organic phosphoric acid represented by the formula (1) or (2), wherein the hydrogen atom is removed from at least one OH group thereof:

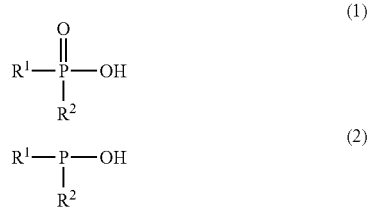

wherein —$R^1$ and —$R^2$ each represent a group selected from —R, —OR, —OH and —H, and at least one of —$R^1$ and —$R^2$ is —R or —OR provided that R is a C1 to C22 organic group.

Metal atom (C): one metal atom or more selected from the group consisting of aluminum, gallium and iron.

In the structure (A), the inorganic phosphoric acid includes orthophosphoric acid or condensed phosphoric acids such as metaphosphoric acid or pyrophosphoric acid, among which orthophosphoric acid is preferable in respect of property. In the structure (B), the organic phosphoric acid represented by the general formula (1) or (2) includes phosphonic acid, monophosphonate, phosphinic acid, monophosphate, diphosphate, monophosphite and diphosphite or a mixture thereof, preferably phosphonic acid.

The organic group R in the organic phosphoric acid is preferably an alkyl group such as methyl, ethyl, n-propyl, iso-propyl, n-butyl, iso-butyl, tert-butyl, n-hexyl, 2-ethylhexyl, octyl, dodecyl and octadecyl, and an aryl group such as phenyl and 3-methylphenyl, to which an amino group, alkoxy group, carbonyl group, alkoxycarbonyl group, carboxylic acid group, halogen atom such as chloro group, phosphonic acid group, and sulfonic acid group may be added.

From the viewpoint of performance and/or cost, the metal atom (C) is preferably aluminum. For the purpose of improving selectivity and other performance, the metal atom (C) may contain a small amount of metal atoms other than aluminum, gallium and iron. It is not always necessary that all metal atoms (C) contained in the catalyst are bonded to the structure (A) or (B), and therefore, a part of the metal atoms (C) may be present in the form of metal oxide, metal hydroxide etc.

Another preferable example of the weakly acidic catalyst of the invention is a molded, heterogeneous catalyst containing aluminum orthophosphate, preferably having a pore diameter of 6 to 100 nm, a pore capacity of 0.46 ml/g or more, and an acid content of 0.40 mmol/g or more.

The process for producing the weakly acidic catalyst in the present invention includes a precipitation method, a method of impregnating a metal oxide or hydroxide with an inorganic phosphoric acid and an organic phosphoric acid, and a method of replacing an inorganic phosphoric acid group of an inorganic aluminum phosphate gel by an organic phosphoric acid group, among which the precipitation method is preferable.

In preparing the catalyst of the present invention, a support having a large surface area may coexist to give the catalyst supported thereon. As the support, silica, alumina, silica alumina, titania, zirconia, diatomaceous earth, activated carbon etc. can be used. When the support is used in excess, the content of the active component is decreased and in consequence the activity is lowered, and thus the proportion of the support in the catalyst is preferably not higher than 90 wt %.

[Step 5]

Step 5 is a step of separating the product discharged from the outlet of a reactor in step 4 into oil and aqueous phases. The separation method and conditions therefor are the same as described in step 3. The separated oil phase contains fatty acid alkyl esters, the starting materials and reaction intermediate glycerides as the main components, as well as very small amounts of water, lower alcohols and glycerin. On one hand, the aqueous phase contains glycerin, water and lower alcohols as the main components, and the side product methoxypropanediol is partitioned mainly into the aqueous phase.

When the unreacted lower alcohols remain in the product from the outlet of a reactor in step 4, performance for separating the fatty acid alkyl esters from the glycerin is lowered. For this reason it is more preferable that, as described in step 2, oil/water separation is carried out after the lower alcohols are removed, more preferably by evaporation, from the product discharged from the outlet of the reactor in the step 4 until the content of the lower alcohols in the product from the reactor in the step 4 is reduced to 8 wt % or less, more preferably 5 wt % or less.

In steps thereafter, the operation described above may be preferably carried out repeatedly to increase the rate of addition of fatty acid alkyl esters. The finally obtained fatty acid alkyl esters can be subjected to hydrogenation in a usual manner to produce fatty alcohols. On one hand, the glycerin obtained in the separation step after each reaction is of quality with a lower content of methoxypropanediol in the glycerine feed, but may be further subjected to distillation etc. to produce high-purity glycerin with a further reduced content of methoxypropanediol. In this case, the glycerin fed has a lower content of methoxypropanediol, thus reducing facilities added and simultaneously increasing the yield of glycerin.

[Process for Producing Fatty Alcohols]

The process for producing fatty alcohols according to the present invention is a process wherein the fatty acid alkyl esters obtained by the process of the invention described above are subjected to hydrogenation reaction to give fatty alcohols. As used herein, the fatty alcohols refer to alcohols derived from fats and oils.

In this process, the hydrogenation catalyst used can be a generally known copper-based catalyst or a noble metal-based catalyst such as catalysts based on palladium or platinum. The copper catalyst can include catalysts such as those made of copper-chrome, copper-zinc, copper-iron-aluminum, copper-silica, etc.

The hydrogenation reaction can be carried out in the presence of a hydrogenation catalyst in any generally used reaction systems such as a fluidized bed system or a fixed bed system.

When the hydrogenation reaction is carried out in a fluidized bed system, the amount of the hydrogenation catalyst can be selected arbitrarily in such a range as to achieve practical reaction yield, depending on reaction temperature and reaction pressure, and is preferably 0.1 to 20 wt % based on the fatty acid alkyl esters. The reaction temperature is preferably 160 to 350° C., more preferably 200 to 280° C. The reaction pressure is preferably 0.1 to 35 MPa, preferably 3 to 30 MPa.

When the hydrogenation reaction is continuously carried out in a fixed bed system, the hydrogenation catalyst is molded preferably in a cylindrical, pellet or spherical form. The reaction temperature is preferably 130 to 300° C., more preferably 150 to 270° C., and the reaction pressure is preferably 0.1 to 30 MPa. In consideration of productivity and reactivity, the LHSV can be determined arbitrarily depending on the reaction conditions.

EXAMPLES

The following examples further describe and demonstrate embodiments of the present invention. The examples are given solely for the purpose of illustration and are not to be construed as limitations of the present invention.

Catalyst Production Example 1

9.9 g ethylphosphonic acid, 27.7 g of 85% orthophosphoric acid, and 112.5 g aluminum nitrate.9$H_2O$ were dissolved in 1000 g water. Aqueous ammonia was added dropwise to this mixed solution at room temperature until the pH was increased to 5. During this step, gelled white precipitates were formed. The precipitates were filtered off, washed with water, dried at 110° C. for 15 hours and pulverized to a size of 60-mesh or less. Alumina sol was added in a final content of 10% to the pulverized catalyst, and the catalyst was extrusion-molded into 1.5-mmϕ pieces. These pieces were calcinated at 250° C. for 3 hours to give a molded catalyst consisting of a solid acid catalyst (referred to hereinafter as catalyst 1). The weak acid point of the resulting catalyst was 1 mmol/g, and the strong acid point was below the limit of detection.

Reference Example 1

Two tube reactors each having an inner diameter of 35.5 mmϕ and a length of 800 mmH, having a tube of 6 mm in inner diameter for temperature measurement in the axial direction, were connected in series and each tube was packed with 500 cc catalyst 1. Refined coconut oil having an acid value of 5.8 was used as the fats and oils and fed together with liquid methanol into the top of the reactor and reacted at a reaction temperature of 170° C. at an LHSV of 0.4, at a reaction pressure of 3.0 MPa-G. The molar amount of methanol fed was 10 times as much as the molar amount (calculated as triglycerides) of the fats and oils. The methyl ester in the oil layer of the reaction solution was 85 wt %. Thereafter, the methanol in the reaction solution was evaporated, and then the reaction mixture was washed with water and left for separation. 180 g of the oil layer thus obtained was reacted again with liquid methanol in the molar amount being 10 times as much as the molar amount (calculated as triglycerides) of the fats and oils by using 9 g of the catalyst 1 at a temperature of 170° C. at a pressure of 1.6 MPa in an autoclave. The concentration of glycerin in the starting oil layer was 0.03 wt %. As a result of analysis of the reaction product obtained after the reaction for 4 hours, the methyl ester in the oil phase was 97 wt %.

Reference Example 2

Two tube reactors each having an inner diameter of 35.5 mmϕ and a length of 800 mmH, having a tube of 6 mm in inner diameter for temperature measurement in the axial direction, were connected in series and each tube was packed with 500 cc catalyst 1. Refined coconut oil having an acid value of 5.8 was used as the fats and oils and fed together with liquid methanol into the top of the reactor and reacted at a reaction temperature of 170° C. at an LHSV of 0.4, at a reaction pressure of 3.0 MPa-G. The molar amount of methanol fed was 10 times as much as the molar amount (calculated as triglycerides) of the fats and oils. The methyl ester in the oil layer of the reaction solution was 85 wt %. Thereafter, the methanol in the reaction solution was evaporated, and then the reaction mixture was washed with water and left for separation, followed by adding glycerin at a final concentration of 1.0 wt % to the resulting separated oil layer. 180 g of the oil layer was reacted again with liquid methanol in the molar amount being 10 times as much as the molar amount (calculated as triglycerides) of the fats and oils by using 9 g of the catalyst 1 at a temperature of 170° C. at a pressure of 1.6 MPa in an autoclave. As a result of analysis of the reaction product obtained after the reaction for 7 hours, the methyl ester in the oil phase was 97 wt %.

From the results in Reference Examples 1 and 2, it was found that when the amount of glycerin brought into the second-stage reaction is increased, the reaction rate is decreased. It follows that when the amount of glycerin brought into the second-stage reaction is high, the reaction temperature should be raised or the amount of the catalyst should be increased in order that the reaction rate is made equal to the reaction rate in the same case as above except that the amount of glycerin brought into the second-stage reaction is low. When the amount of the catalyst is increased, higher costs result.

Example 1

A tube reactor of 237.2 mmφ in inner diameter was packed with 45000 cc catalyst 1. Refined coconut oil having an acid value of 5.8 was used as the fats and oils and fed together with liquid methanol into the top of the reactor and reacted at a reaction temperature of 170° C. at an LHSV of 0.4, at a reaction pressure of 3.0 MPa-G. The molar amount of methanol fed was 10 times as much as the molar amount (calculated as triglycerides) of the fats and oils. The reaction solution was fed to an evaporator, and the methanol was evaporated at a pressure of 760 mmHg at 150° C. The content of methanol in the oil phase was 1.1 wt %. Thereafter, the liquid sample was left and thereby separated at 50° C. into an oil phase and an aqueous phase. The methyl ester in the resulting oil phase was 79 wt %, and the glycerin concentration was 0.3 wt %. 180 g of the oil layer was reacted again with liquid methanol in the molar amount being 10 times as much as the molar amount (calculated as triglycerides) of the fats and oils by using 9 g of the catalyst 1 in an autoclave. The temperature was 170° C., the pressure was 1.6 MPa, and the reaction time was 6 hours. The resulting reaction product was separated into oil and aqueous phases and analyzed, and as a result, the methyl ester in the oil phase was 97 wt %, and the degree of formation of methoxypropanediol (MPD) as a side product was 2 wt % relative to glycerin.

Comparative Example 1

A tube reactor of 237.2 mmφ in inner diameter was packed with 45000 cc catalyst 1. Refined coconut oil having an acid value of 5.8 was used as the fats and oils and fed together with liquid methanol into the top of the reactor and reacted at a reaction temperature of 170° C. at an LHSV of 0.4, at a reaction pressure of 3.0 MPa-G. The molar amount of methanol fed was 10 times as much as the molar amount (calculated as triglycerides) of the fats and oils. The reaction solution was fed to an evaporator, and the methanol was evaporated at a pressure of 760 mmHg at 80° C. The content of methanol in the oil phase was 8.2 wt %. Thereafter, the liquid sample was left and thereby separated at 50° C. into an oil phase and an aqueous phase. The methyl ester in the resulting oil phase was 79 wt %, and the glycerin concentration was 1.0 wt %. 180 g of the oil layer was reacted again with liquid methanol in the molar amount being 10 times as much as the molar amount (calculated as triglycerides) of the fats and oils by using 9 g of the catalyst 1 in an autoclave. The temperature was 190° C., the pressure was 2.4 MPa, and the reaction time was 6 hours. The resulting reaction product was separated into oil and aqueous phases and analyzed, and as a result, the methyl ester in the oil phase was 97 wt %, and the degree of formation of methoxypropanediol (MPD) as a side product was 5 wt % relative to glycerin.

From this result, it was found that when the amount of glycerin brought into the second-stage reaction is increased and when the reaction temperature is increased to attain the same yield of methyl ester in the same retention time, the amount of the side product methoxypropanediol is increased to decrease the yield of glycerin.

Example 2

The oil phase obtained in Example 1 was further reacted in the same reactor thereby giving an oil phase containing 99.4 wt % fatty acid methyl ester. Water was added in a final content of 2 wt % to the resulting oil phase, then stirred for 30 minutes and left for 1 hour to separate it into oil and aqueous phases, followed by rectification to give fatty acid methyl esters. Then, the resulting fatty acid methyl esters were subjected to hydrogenation reaction in a fixed bed reactor having a column packed with 259 mL titania-supported copper-zinc catalyst (composition: Cu=35%, Zn=1.8%, 50% TiO$_2$ catalyst, in the form of 3.2 mmφ×3.2 mm cylinder) to give fatty alcohols. The hydrogenation reaction was conducted under the conditions of a pressure of 19.6 MPa and a temperature of 220° C. The feed rate of fatty acid methyl esters was 187 mL/h, and the flow rate of hydrogen was 414 mL/h.

The invention claimed is:
1. A process for producing a fatty alkyl ester and glycerin, comprising:
(1) reacting fats and oils with a C1 to C5 lower alcohol;
(2) removing the lower alcohol from the outlet product of step 1 until the lower alcohol content is reduced to 2 wt % or less;
(3) separating the product obtained in step 2 into an oil phase and an aqueous phase at 70° C. or lower to obtain an oil phase having a glycerin content of 0.6 wt. % or less;
(4) reacting the oil phase obtained in step 3 with a lower alcohol in the presence of an acid catalyst; and
(5) separating the outlet product of step 4 into an oil phase and an aqueous phase to obtain an fatty acid alkyl ester (s) and glycerin
wherein said acid catalyst has a structure (A) of an inorganic phosphoric acid wherein a hydrogen atom is removed from at least one OH group thereof, a structure (B) of an organic phosphoric acid represented by formula (1) or (2)

wherein a hydrogen atom is removed from at least one OH group thereof
wherein —R$^1$ and —R$^2$ each represent a group selected from —R, —OR, and —H and at least one of —R$^1$ and —R$^2$ is —R or —OR provided that R is a C$_{1-22}$ organic group, and a metal atom (C).

2. The process according to claim 1, wherein the lower alcohol is removed by evaporation in step 2.

3. The process according to claim 1, wherein the separation step 3 is carried out at 60° C. or less.

4. The process according to claim 1, wherein the acid catalyst of step (4) is a molded product of a heterogeneous catalyst comprising aluminum orthophosphate.

5. A process for producing a fatty alcohol(s) comprising:
(a) producing a fatty alkyl ester and glycerin, comprising:
(1) reacting fats and oils with a C1 to C5 lower alcohol;
(2) removing the lower alcohol from the outlet product of step 1 until the lower alcohol content is reduced to 2 wt % or less;

(3) separating the product obtained in step 2 into an oil phase and an aqueous phase at 70° C. or lower to obtain an oil phase having a glycerin content of 0.6 wt. % or less;
(4) reacting the oil phase obtained in step 3 with a lower alcohol in the presence of an acid catalyst; and
(5) separating the outlet product of step 4 into an oil phase and an aqueous phase to obtain an fatty acid alkyl ester(s) and glycerin wherein said acid catalyst has a structure (A) of an inorganic phosphoric acid wherein a hydrogen atom is removed from at least one OH group thereof, a structure (B) of an organic phosphoric acid represented by formula (1) or (2)

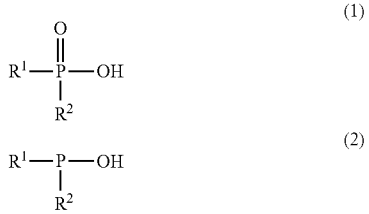

wherein a hydrogen atom is removed from at least one OH group thereof wherein —$R^1$ and —$R^2$ each represent a group selected from —R, —OR, and —H and at least one of —$R^1$ and —$R^2$ is —R or —OR provided that R is a $C_{1-22}$ organic group, and a metal atom (C);

(b) reacting the fatty alkyl ester obtained from (a) with hydrogen to produce a fatty alcohol.

6. The process according to claim 1, wherein said acid catalyst has a strong acid point of not higher than 0.2 mmol/g-cat and a weak acid point of not less than 0.3 mmol/g-cat.

7. The process according to claim 1, wherein said lower alcohol comprises methanol.

8. The process according to claim 1, wherein a molar ratio of lower alcohol to fats and oils calculated as triglycerides is 1.5 or more.

9. The process according to claim 1, wherein a molar ratio of lower alcohol to fats and oils calculated as triglycerides is 50 or less.

10. The process according to claim 1, wherein a molar ratio of lower alcohol to fats and oils calculated as triglycerides is 15 or less.

11. The process according to claim 1, wherein a reaction temperature in step 1 is 50° C. to 230° C.

12. The process according to claim 1, wherein step 1 is conducted in the presence of a catalyst in an amount of from 1 to 20 wt. % when said reaction is carried out in a vessel type reactor.

13. The process according to claim 1, wherein step 1 is carried out in a fixed bed reactor at a liquid hourly space velocity based on said fats and oils of not lower than 0.02/hr.

14. The process according to claim 1, wherein step 1 is carried out at a reaction pressure of 0.1 to 10 MPa.

15. The process according to claim 1, wherein said oil phase in step 3 has a glycerin content of 0.4 wt. % or less.

16. The process according to claim 1, wherein said metal is aluminum.

17. The process according to claim 1, wherein said acid catalyst is a solid acid catalyst.

18. The process according to claim 1, wherein —R is selected from the group consisting of methyl, ethyl, n-propyl, iso-propyl, n-butyl, iso-butyl, tert-butyl, n-hexyl, 2-ethylhexyl, octyl, dodecyl, octadecyl, phenyl and 3-methylphenyl.

19. The process according to claim 18, wherein —R is substituted with at least one group selected for the group consisting of an amino group, an alkoxy group, a carbonyl group, an alkoxycarbonyl group, a carboxylic acid group, a halogen atom, a phosphonic acid group, and a sulfonic acid group.

* * * * *